United States Patent [19]

Richard et al.

[11] Patent Number: 5,227,521

[45] Date of Patent: Jul. 13, 1993

[54] PREPARATION OF TRIALKYLACETIC ACIDS, PARTICULARLY OF PIVALIC ACID, USING LEWIS ACID CATALYSTS

[75] Inventors: Michael A. Richard, Foster City; William A. Sanderson, Portola Valley, both of Calif.

[73] Assignee: Catalytica Inc., Mountain View, Calif.

[21] Appl. No.: 683,439

[22] Filed: Apr. 9, 1991

[51] Int. Cl.$^5$ .................. C07C 51/14; C07C 51/377; C07C 53/122

[52] U.S. Cl. ..................... 562/521; 203/66; 562/599

[58] Field of Search ............. 562/521; 260/413, 403, 260/400, 408, 404

[56] References Cited

U.S. PATENT DOCUMENTS

| | | | |
|---|---|---|---|
| 2,135,459 | 11/1938 | Loder | 562/521 |
| 2,831,877 | 4/1958 | Koch et al. | 260/413 |
| 2,967,873 | 1/1961 | Koch et al. | 260/410.9 |
| 3,061,621 | 10/1962 | Koch et al. | 260/413 |
| 3,068,256 | 12/1962 | Roming | 260/413 |
| 3,099,687 | 7/1963 | Rohlffs et al. | 562/521 |
| 3,527,779 | 9/1970 | Paulis et al. | 260/413 |
| 4,256,913 | 3/1981 | Jung et al. | 560/521 |
| 4,262,138 | 4/1981 | Gelbein | 560/233 |
| 4,311,851 | 1/1982 | Jung et al. | 560/233 |

FOREIGN PATENT DOCUMENTS

| | | |
|---|---|---|
| 0249976 | 12/1987 | European Pat. Off. . |
| 1167116 | 10/1969 | United Kingdom . |
| 1174209 | 12/1969 | United Kingdom . |

*Primary Examiner*—Arthur C. Prescott
*Attorney, Agent, or Firm*—Morrison & Foerster

[57] ABSTRACT

This invention is a process for the production of trialkyl acetic acids, particularly of pivalic acid, from branched olefins, particularly isobutene, and carbon monoxide using catalytic amounts of a Lewis acid such as boron trifluoride.

5 Claims, No Drawings

PREPARATION OF TRIALKYLACETIC ACIDS, PARTICULARLY OF PIVALIC ACID, USING LEWIS ACID CATALYSTS

FIELD OF THE INVENTION

This invention is a process for the production of trialkyl acetic acids, particularly of pivalic acid, from branched olefins, particularly isobutene, and carbon monoxide using catalytic amounts of a Lewis acid such as boron trifluoride.

BACKGROUND OF THE INVENTION

Of the trialkylacetic acids, pivalic acid [$(CH_3)_3CCOOH$] is one of the most widely used. It is a fine chemical suitable as a starting material for various agrichemicals, pharmaceuticals, aroma chemicals, specialty chemicals, and polymer additives. Trialkylcarboxylic acids are typically made in large scale commercial amounts using a non-catalytic process involving substantial amounts of highly corrosive liquid acidic reactant, often containing boro trifluoride. The acidic reactants are typically present in molar amounts equal to or greater than that of the branched olefin feed.

Typical of this technology is U.S. Pat. No. 3,068,256 to Roming. This patent describes a process in which the material characterized as the catalyst (liquid mineral acids having a specific gravity greater than 1.25, e.g., $H_2SO_4$, $BF_3 2H_2O$, or mixtures of $BF_3 2H_2O$ with $H_2SO_4$ or $H_3PO_4$) is used in amounts approximately stoichiometric with the olefinic feed. However, this catalytic material must be recovered by hydrolysis of an intermediate complex generated by stoichiometric reaction of olefin, carbon monoxide, and the acid. Consequently, the disclosed process requires a large catalyst inventory; it also requires expensive materials of construction suitable for handling that large corrosive acid catalyst inventory. Furthermore, the hydrolysis step is very difficult to control if optimal regeneration of the acid catalyst to its most active state is desired.

In summary, the process disclosed in the Roming patent is not truly catalytic in nature in the sense that large amounts of the acid along with the feed olefin, carbon monoxide, and water are reacted to form the product carboxylic acid. The catalyst separation and recovery steps are complex.

Similarly, U.S. Pat.No. 3,061,621 to Koch et al, discloses a process for the production of carboxylic acids from olefins and carbon monoxide using a molar excess of an acid catalyst selected from orthophosphoric acid, derivatives of orthophosphoric acid, higher polyphosphoric acids, and their mixtures. This process involves use of large amounts of the catalyst which must be regenerated and recycled in a complicated series of steps.

The process shown in U.S. Pat. No. 2,831,877 to Koch et al. involves two separate steps. In the first step, feed olefin and carbon monoxide are contacted with very strong, and potentially very corrosive, acid catalysts. Suitable acid catalysts are said to include 90% to 100% sulfuric acid, anhydrous HF, anhydrous HF-$BF_3$, chlorosulfonic acid, and fluorosulfonic acid. The resulting intermediate formed upon stoichiometric reaction of the acid, olefin, and carbon monoxide is hydrolyzed with water to liberate the product carboxylic acid. The catalyst must be regenerated to its anhydrous form prior to re-use in the process. This step entails treatment of a very corrosive stream containing significant amounts of water. Clearly, costly corrosion-resistant materials of construction are necessary. A preferable process would entail the use of a catalyst having a substantially less corrosive catalyst and a more economical catalyst recovery routine.

A further U.S. patent to Koch et al. U.S. Pat. No. 2,967,873) describes a process for the production of alkyl esters of carboxylic acids. The process involves two steps. The first step involves reaction of an olefin containing at least six carbon atoms with carbon monoxide using approximately a stoichiometric amount of an acid catalyst. The acid catalyst is said to contain boron trifluoride in the form of hydroxy- and alkoxy-fluoboric acid, potentially with complexed alcohols. The second step is the alcoholysis of the intermediate complex formed in the first step to produce the desired ester.

A process suffering from a highly corrosive operating environment and requiring a large excess of wet hydrofluoric acid (as the catalyst) is disclosed in GB 1,167,116 assigned to Shell Internationale Research Maatschappij N.V. The process involves the one step synthesis of carboxylic acids by reacting a four-to-ten carbon atom branched olefin with carbon monoxide in the presence of a large excess of hydrofluoric acid (preferably a hydrogen fluoride/olefin ratio of about 10:1) and about a 50% molar excess of water. As with a number of processes discussed above, this process has a serious disadvantage in that the hydrofluoric acid must be separated from a product mixture which contains excess water. Hydrofluoric acid is also extremely corrosive and toxic.

A process similar to that disclosed in GB 1,167,116 is shown in GB 1,174,209, also assigned to Shell. GB '209 also discloses steps for recovery and recycle of at least a portion of the hydrofluoric acid catalyst.

Another process using an acid catalyst in an amount more than equimolar to the olefin feed is found in U.S. Pat. No. 3,527,779 to Paulis et al. That process uses a boron trifluoride-water phosphoric acid catalyst which is said to be less corrosive than hydrofluoric acid or boron trifluoride hydrate and more readily recovered from the carboxylic acid product. The catalyst is, however, used in molar excess to the feed olefin. It may be recovered in a subsequent step for recycle.

Much of the literature discussed here is limited to the reaction of higher olefins to produce saturated carboxylic acids. In U.S. Pat. No. 4,256,913 to Jung et al. the disclosed process is limited to the carbonylation of lower, nonbranched olefins, ethylene and propylene, to the corresponding carboxylic acids. A description for the recovery and reuse of the catalyst is not shown.

The U.S. Pat. No. 4,311,851 to Jung et al. discloses a process for producing carboxylic acid esters and for recovering and reconstituting the boron trifluoride-alcohol catalyst. This process involves a very complicated series of steps for recovery of the catalyst: the operation is carried out until one-half of the alcohol feed is consumed, any remaining free $BF_3$ is vaporized, additional alcohol is added to the reaction medium, and the reaction mixture is distilled. An azeotrope of the alcohol and the product ester is the distillation product. Heavy by-products are removed from the distillation bottoms by solvent extraction. The treated bottoms are mixed with added $BF_3$ to form the original catalyst mixture. A simpler process would be desirable.

The U.S. Pat. No. to Gelbein (No. 4,262,138) is a variation of the process shown in Jung et al '851 discussed above, but also appears to be specific to the carbonylation of ethylene and propylene.

A published European Patent Application (No. 0,249,976) assigned to BASF AG discloses a process for the production of carboxylic acids from the reaction of an olefin with carbon monoxide and water over a zeolite catalyst or a modified zeolite catalyst. This process uses a catalyst which is easy to handle and has low corrosivity. However, the process exemplifies high yields of carboxylic acids only at high temperatures and pressures.

Our process is one which uses Lewis acids in amounts less than or equal to the amount of olefin fed to the synthesis step. None of the materials cited above utilize catalytic amounts in such frugal amounts in producing trialkylacetic acids.

SUMMARY OF THE INVENTION

This invention is a Lewis-acid catalyzed process for producing certain trialkylacetic acids from corresponding branched olefins, carbon monoxide, and water according to the following reaction:

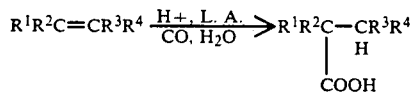

where $R^1$, $R^2$=alkyl or substituted alkyl; $R^3$, $R^4$=H, alkyl, or substituted alkyl. The Lewis acid is used in amounts less than equimolar to the amount of branched olefin fed to the process.

DESCRIPTION OF THE INVENTION

This invention broadly is a Lewis acid catalyzed process for producing certain trialkylacetic acids from corresponding branched olefins, carbon monoxide, and water according to the following reaction:

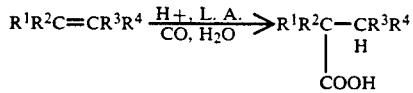

where $R^1$, $R^2$=H, alkyl, or substituted alkyl; $R^3$, $R^4$=H, alkyl, or substituted alkyl; if $R^1$ and $R^3$ are H, then $R^2$ and $R^4$ must be alkyl or substituted alkyl and at least one of $R^2$ and $R^4$ must be branched. Each of $R^1$, $R^2$, $R^3$, and $R^4$ may be the same or different than the other substituent moieties. Preferably, $R^1$, $R^2$, $R^3$, and $R^4$ are independently $C_{1-5}$ linear or branched alkyl groups possibly substituted with inorganic moieties such as Si, N, P, or S which do not tend to form ionic species in the water-containing reaction medium. Most preferred is the situation in which $R^1$ and $R^2$ are $CH_3$ and $R^3$ and $R^4$ are H.

This invention also includes the specific overall process of producing pivalic acid from isobutene, carbon monoxide, and water:

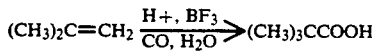

Lewis Acids

The catalyst used in this process comprises one or more Lewis acids. A Lewis acid is a molecule which can form another molecule or an ion by forming a complex in which it accepts two electrons from a second molecule or ion. Typical strong Lewis acids include boron halides such as $BF_3$, $BCl_3$, $BBr_3$, and $BI_3$; antimony pentafluoride ($SbF_5$); aluminum halides ($AlCl_3$ and $AlBr_3$); titanium halides such as $TiBr_4$, $TiCl_4$, and $TiCl_3$; zirconium tetrachloride ($ZrCl_4$); phosphorus pentafluoride ($PF_5$); iron halides such as $FeCl_3$ and $FeBr_3$; and the like. Weaker Lewis acids such as tin, indium, bismuth, zinc, or mercury halides are also acceptable. Preferred Lewis acids are $SbF_5$, $AlCl_3$, and $BF_3$; most preferred is $BF_3$. It should be apparent that some selection of Lewis acid from this list is necessary depending upon such factors as the amount of water present, the trialkylacetic acid desired, etc. since there will be a tendency for the Lewis acid to hydrolyze in competition with the reaction forming the carboxylic acid.

Process Conditions

The Lewis acid, water, and the carbon monoxide may be added in convenient forms (gas, liquid, or solid) to the reaction medium. Some care should be exercised in contacting the water reactant and the Lewis acid, e.g., the Lewis acid desirably is not initially placed in contact with the water, the water is instead added last to the medium. In contrast to prior art processes, the Lewis acid is present in amounts substantially less than a molar equivalent to the branched olefin. Isobutene or other branched olefins are added to the reactor with the required water. The reaction is more facile at elevated temperature, e.g., at 65° C. or higher, but at which the reaction medium is still in the liquid phase. Excellent results have been achieved at temperatures between 100° C. and 150° C. A temperature of about 125° C. is most preferred.

The process may be operated using one or more solvents as the reaction medium. Solvents such as linear or cyclic alkanes are desirable in that they are unreactive and are often easily separated from the product organic acids. Materials such as isobutane are especially desirable because they are readily separable from products such as the substantially heavier trialkylacetic acids, e.g., isobutane (bp. −12° C.) may be removed from the product pivalic acid (bp. 163° C.) by flashing. Further, it dissolves both the isobutene reactant and is essentially nonreactive toward the $BF_3$ catalyst.

The invention has been disclosed by direct description. Below may be found a number of examples showing various aspects of the invention. The examples are only examples of the invention and are not to be used to limit the scope of the invention in any way.

EXAMPLES

The following Examples show the synthesis of trialkylacetic acids, particularly of pivalic acid, from isobutene, and the benefits of the catalyst system. In each example, the autoclave was evacuated and pressurized with boron trifluoride. The isobutane solvent was then added and the stirrer started. The autoclave was pressurized to about 1200 psi with carbon monoxide and heated to the reaction temperature. Isobutene reactant (dissolved in isobutane solvent) was co-added with water.

Example 1

This example shows the use of boron trifluoride at a lower pressure and the production of pivalic acid.

The boron trifluoride was added by pressuring the reactor to 10 psi. The reaction temperature was 95° C. Pivalic acid was produced in a minor amount (approximately 10%) with the balance of the product being dimers and trimers of isobutene.

Example 2

This example shows the production of pivalic acid using a slightly higher temperature.

The boron trifluoride was added by pressuring the reactor to 10 psi. The reaction temperature was 125° C. An isobutene/isobutane mixture (31 v/v isobutene containing 13.36 g isobutene) was then added. An amount (12.2 g) of a yellow liquid product was recovered.

The product contained 80% (by mole) pivalic acid.

Example 3

This example shows the production of pivalic acid using both higher temperature and higher boron trifluoride pressure.

The boron trifluoride was added by pressuring the reactor to 65 psi. The reaction temperature was 127° C. An isobutene/isobutane mixture (29.36 v/v isobutene containing 24.6 g isobutene) was then added. An amount (18.62 g) of a brown liquid was recovered.

The product contained 88.4% (by mole) pivalic acid.

This invention has been described using examples to show preferred embodiments. It will be apparent to those skilled in the art that modifications and changes may be made which still fall within the spirit and scope of the attached claims.

We claim as our invention:

1. A process for the production of trialkylacetic acids comprising the steps of:
   a. contacting a branched olefin of the formula:

$$R^1R^2C=CR^3R^4$$

where $R^1$, $R^2$ are H or alkyl and $R^3$, $R^4$ are H or alkyl (if $R^1$ and $R^3$ are H, then $R^2$ and $R^4$ must be alkyl and at least one of $R^2$ and $R^4$ must be branched) with carbon monoxide, and a catalytic amount of a substantially anhydrous Lewis acid catalyst system consisting essentially of a catalytic amount of boron trifluoride which catalytic amount is less than a molar amount to the branched olefin present and then only with an amount of water stoichiometric for the branched olefin, and, to produce trialkylacetic acids of the formula:

$$R^1R^2C-CHR^3R^4$$
   $$|$$
   $$COOH$$

and
   b. recovering the trialkylacetic acid.

2. The process of claim 1 where $R^1$, $R^2$, $R^3$, and $R^4$ are independently $C_{1-5}$ linear or branched alkyl groups.

3. The process of claim 2 where $R^1$ and $R^2$ are $-CH_3$ and $R^3$ and $R^4$ are H.

4. A process for the production of pivalic acid comprising the steps of
   a. contacting isobutene and carbon monoxide with a substantially anhydrous Lewis acid catalyst system consisting essentially of a catalytic amount of boron trifluoride in an amount less than equimolar to the isobutene present and then only with an amount of water stoichiometric to the isobutene to produce pivalic acid, and
   b. recovering the pivalic acid.

5. The process of claim 4 where the contacting step takes place in the presence of isobutane.

* * * * *